US006462002B2

(12) United States Patent
Saxena et al.

(10) Patent No.: US 6,462,002 B2
(45) Date of Patent: Oct. 8, 2002

(54) MONOHYDRIC ALCOHOL-FREE TRANSPARENT MOISTURIZING BAR SOAP WITH PLASTIC PACKAGING MOLD

(75) Inventors: Rahul Saxena, East Grand Rapids, MI (US); William M. Luke, Grand Rapids, MI (US)

(73) Assignee: Access Business Group International LLC, Ada, MI (US)

(*) Notice: Subject to any disclaimer, the term of this patent is extended or adjusted under 35 U.S.C. 154(b) by 0 days.

(21) Appl. No.: 09/873,562

(22) Filed: Jun. 4, 2001

(65) Prior Publication Data

US 2001/0034311 A1 Oct. 25, 2001

Related U.S. Application Data

(62) Division of application No. 09/386,127, filed on Aug. 30, 1999, now Pat. No. 6,297,205.

(51) Int. Cl.[7] .................................................. A61K 7/50

(52) U.S. Cl. ....................... 510/141; 510/140; 510/147; 510/144; 510/152; 510/155

(58) Field of Search ................................ 510/140, 141, 510/147, 144, 152, 155

(56) References Cited

U.S. PATENT DOCUMENTS

| | | | | |
|---|---|---|---|---|
| 2,005,160 A | | 6/1935 | Pape | |
| 2,820,768 A | | 1/1958 | Fromont et al. | |
| 2,970,116 A | | 1/1961 | Kelly et al. | |
| 3,562,167 A | | 2/1971 | Kamen et al. | |
| 3,864,272 A | | 2/1975 | Toma et al. | |
| 4,290,904 A | | 9/1981 | Poper et al. | |
| 4,406,364 A | * | 9/1983 | Bronander, Jr. | 206/77.1 |
| 4,754,874 A | * | 7/1988 | Haney | 206/77.1 |
| 4,758,370 A | | 7/1988 | Jungermann et al. | |
| 4,879,063 A | | 11/1989 | Wood-Rethwill et al. | |
| 5,496,489 A | | 3/1996 | Dussault et al. | |
| 5,529,714 A | | 6/1996 | Tokosh | |
| 5,786,311 A | | 7/1998 | Zyngier et al. | |
| 5,869,437 A | | 2/1999 | Wolfersberger | |
| 6,184,191 B1 | | 2/2001 | Wolfersberger | |

FOREIGN PATENT DOCUMENTS

| | | |
|---|---|---|
| EP | 0335026 | 3/1988 |

* cited by examiner

*Primary Examiner*—Necholus Ogden
(74) *Attorney, Agent, or Firm*—Warner Norcross & Judd LLP

(57) ABSTRACT

A monohydric alcohol-free, transparent, moisturizing bar soap having a high humectant solvent content. The formulation includes: (i) from about 38% to about 96% of one or more humectant solvents and (ii) from about 3% to about 20% of insoluble and/or soluble fatty acid soaps, with at least about 3% insoluble fatty acid soap. The weight ratio of humectant solvent to insoluble fatty acid soap ranges from about 3:1 to about 23:1. The bar soap has a standardized wear rate of less than about 15% and a hardness of from about 30 to about 100 hardness units. The transparent solid bar soap may be manufactured by a "hot pour" process with conventional batch mixing equipment designed for relatively moderate temperatures; accordingly, the bar soap may be packaged for final consumer use in the mold in which it was formed.

20 Claims, No Drawings

MONOHYDRIC ALCOHOL-FREE TRANSPARENT MOISTURIZING BAR SOAP WITH PLASTIC PACKAGING MOLD

This is a divisional of application Ser. No. 09/386,127, filed Aug. 30, 1999 now U.S. Pat. No. 6,297,205.

BACKGROUND OF THE INVENTION

The present invention relates to transparent bar soaps, and more particularly to moisturizing transparent bar soaps essentially free of monohydric alcohol and having a high humectant content.

A personal bar soap is characterized as "moisturizing" if the bar soap contains an agent that helps retain moisture in the skin (i.e., a "humectant"). Humectants (such as glycerin) help prevent the skin from excessively drying during the wash process. Excessive skin drying can result in raw, red, chapped, irritated, itchy, or cracked skin—especially for those with sensitive skin or during the winter months when indoor air heating can create very dry air that contributes to skin drying. Generally, the more humectant that is present in the bar soap, the better the moisturizing attributes of the soap.

Consumers consider a transparent bar soap having a high humectant content as a premium bar soap, not only because of the enhanced moisturizing properties, but also because the humectant content significantly increases the cost of the bar soap. However, increasing the amount of glycerin humectant to provide better moisturization for a transparent bar soap generally decreases the desirable hardness, resistance-to-wear, and foaming attributes of the bar. For example, U.S. Pat. No. 5,786,311 issued Jul. 28, 1998 to Zyngier entitled "Monohydric Alcohol-Free Process for Making a Transparent Pour Molded Personal Cleansing Bar" states that the amount of humectant (such as glycerin and propylene glycol) in the transparent bar soap should not exceed about 37%. (Column 7, lines 6–9.) Further, although the hardness and detergency of a bar soap can be improved by increasing the fatty acid soap content, that component also tends to negatively affect the transparency of the bar soap.

Soap formulators have addressed these problems by adding significant amounts of monohydric alcohol (e.g., ethanol) to dissolve the fatty acid soap. However, monohydric alcohols contribute to skin dryness. Also, bars containing monohydric alcohol typically display increased weight loss due to evaporation of the volatile alcohol. Specialized and expensive explosion-proof process equipment is also required with monohydric alcohol-containing soap formulations, due to the volatile and explosive nature of monohydric alcohols.

The fatty acid soap component of a bar soap can be made in situ by the well-known saponification process—that is, the reaction of triglyceride with caustic to produce fatty acid soap and glycerin. However, the high temperature associated with the saponification process frequently causes undesirable discoloration of soap bars.

SUMMARY OF THE INVENTION

The aforementioned problems are overcome in the present invention wherein a monohydric alcohol-free transparent bar soap formulation includes a high level of humectant solvent, yet has good hardness and wear characteristics. More specifically, the inventive soap formulation includes from about 38% to about 96% of one or more humectant solvents, such as glycerin and propylene glycol. The formulation also includes from about 3% to about 20% of insoluble and/or soluble fatty acid soaps, so that the amount of insoluble fatty acid soap is at least about 3%. The weight ratio of humectant solvent to insoluble fatty acid soap ranges from about 3:1 to about 23:1. The formulation is substantially free of monohydric alcohol, and produces a transparent solid bar soap having a standardized wear rate of less than about 15% and a hardness of from about 30 to about 100 hardness units, or about 3 mm to 10 mm, where each hardness unit is 1/10 mm penetration into the bar.

The transparent solid bar soap may be manufactured by: (i) forming a liquid homogeneous bar soap mixture that includes the above-described amounts of components and that is substantially free of monohydric alcohol, (ii) transferring the homogeneous liquid mixture to a mold or tray, and (iii) cooling the transferred mixture to form a transparent solid bar soap having a standardized wear rate of less than about 15% and a hardness of from about 30 to about 100 hardness units or about 3 mm to 10 mm where each hardness unit is 1/10 mm penetration into the bar.

The inventive soap formulation provides several advantages. The formulation includes high amounts of humectant solvent to provide superior skin moisturization characteristics; yet, the formulation produces transparent—even clear—bar soaps having wear rates and hardnesses comparable to opaque bar soaps. The formulation produces very light yellow to water-white bar soaps that provide a wide range of color options. During storage, the finished bar soap maintains its transparency without crystallization of the fatty acid soap molecules that can cloud the bar soap. During use, the bar soap formulation does not leave a drying film or greasy residue on the skin.

The inventive process of forming the transparent bar soap also has several advantages. The process uses relatively short batch times and moderate temperatures, thus avoiding the discoloration problems associated with longer batch times and higher temperatures, such as those required for the saponification process of soap manufacture. The process can use a conventional batch mixing tank that is lower in operating, installation, and equipment costs than the specialized explosion proof equipment associated with making soap from saponification processes using alcohol formulations. Further, the process reduces the safety hazard that is a part of processing mixtures above their flashpoint. The soap formulation can be "hot poured" directly to a mold for cooling to form a solid bar. Since the soap may be poured at a relatively low temperature, the mold can be constructed of relatively less expensive materials such as plastic, high density polyethylene (HDPE), polyethylene terephthalate (PET), or polypropylene (PP). Advantageously, using the low temperature molding techniques, and such low cost molds, it is possible to use the mold in which the soap is actually manufactured as the final packaging apparatus marketed to consumers. Further, because the molten soap can be packaged before it actually congeals, the additional congealing time is eliminated from the manufacture of finished product soap bars. Unlike monohydric alcohol-containing soaps, the forming of fatty acid soap crystals is relatively independent of the cooling rate; thus, the inventive formulation does not need to cool slowly to maintain transparency. Also, the bar soap scrap material from the bar soap finishing process can be recycled to the next batch for continuous processing.

These and other objects, advantages, and features of the invention will be more readily understood and appreciated by reference to the detailed description of the preferred embodiment.

DETAILED DESCRIPTION OF THE PREFERRED EMBODIMENT

The attributes of the bar soap formulation of the present invention can be characterized by reference to several categories, such as transparency, hardness, and wear rate, which are described below. The inventive bar soap formulation also includes one or more of the following components: (i) fatty acid soaps, (ii) humectant solvents, (iii) water, (iv) fatty acid soap solubilization aids, and (v) lathering synthetic surfactants, which are also described below. Further, the transparent bar soap can be manufactured using a "hot pour" method without the need for in situ saponification.

Bar Soap Characteristics

It is desirable that a transparent moisturizing bar soap have good performance in the following categories: (1) transparency, (2) hardness, (3) wear rate, (4) foaming, (5) weight loss, (6) stability, and (7) pH.

A bar soap is considered "transparent" if one can read 14 point type font through a ¼ inch thickness of the bar. A bar soap is considered "clear" if one can read 6 point type font through a half-inch thickness of the bar.

The hardness of a bar soap is expressed in "hardness units," which are measured by a Penetrometer at room temperature. Each hardness unit is 1/10 mm. The hardness is represented by the depth traveled in 15 seconds into a bar soap by an ASTM D-1321 needle weighed down by a 50 gram weight. Three readings on an approximately 24-hour old bar are averaged. Acceptable bar soap hardnesses include from about 30 to about 100 hardness units, preferably from about 40 to about 75 hardness units. The hardness of a bar soap formulation depends on numerous factors, including the amount and type of fatty acid soaps and humectant solvents present in the formulation.

The "standardized wear rate" of a bar soap is measured as follows. First, a rectangularly shaped bar of soap weighing 100 (+/−5) grams is cut from a portion of solidified soap that is at least 12 to 24 hours old. The bar is grasped by one hand and placed under a flow of tap water having a temperature of 32 (+/−2) ° C. and a flow rate of 900 (+/−50) milliliters per 20 seconds. While under the tap water flow, the bar is rotated in and by one hand for 20 rotations. The bar is then dried. This procedure is repeated 10 times over a 2- to 3-day period. The "wear rate" is the resulting percentage of weight loss. An acceptable bar soap wear rate is from about 5% to about 15%, preferably less than about 10%.

The "standardized foam volume" of a bar soap is measured as follows. First, one gram of the bar soap composition is dissolved in 99 grams of purified water to form a soap solution. The soap solution is warmed to about 38° C. The warmed solution is poured into a graduated volumetric cylinder attached to a blender. The blender is actuated for 15 seconds to vigorously agitate the soap solution. After agitation, the foam is allowed to subside for 5 to 10 seconds. The volume of foam is then recorded. Acceptable bar soap standardized foam volumes range from about 100 to about 300 milliliters. The foam characteristics of a bar soap can also be subjectively analyzed by a simple wash down with the bar soap. As is known in the art, the foam can be characterized by its flash foam and lather attributes.

Bar soaps are known to lose weight even during non-use periods. The weight loss of a bar soap for a given period is measured as follows. First, two rectangularly shaped bars of 100 (+/−5) grams each are cut from a portion of solidified soap that is at least 12 to 24 hours old. The first bar is placed on a rack at ambient room conditions. The second is place on a rack in an oven at 40° C. After desired periods (e.g., 1-day, 3-day, 1-week, 1-month, and 3-month periods) at the specified temperature, the bars are weighed again. The standardized weight loss is expressed as a percentage of weight loss. The bar exposed to 40° F. temperature is used to calculate the "accelerated weight loss." Exposure for 3 months at 40° F. is exemplary of the expected weight loss of a bar at ambient room conditions for one year. An acceptable bar soap accelerated weight loss for 3 months is from about 2% to about 10%.

Stability data shows that some bar soaps exhibit the negative attribute of "sweating." Sweat may appear as droplets on the surface of the bar soap or as a thin liquid film between the bar and the package, resulting in stickiness. Bars containing high levels of moisturizers have an increased tendency to sweat. Sweating can be reduced to an acceptable level by incorporating appropriate amounts of gelling agents, which are well-known to those of skill in the art.

The acidic or basic nature of the bar is indicated by its pH. The pH of a bar soap is measured by forming a soap solution having one gram of the bar soap composition dissolved in 99 grams of purified water. The pH is measured at 21° C. An acceptable bar soap pH ranges from about 9 to 11, preferably from about 9.1 to about 10.0.

In producing the inventive transparent bar soap, no monohydric alcohol (other than potential trace amounts associated with the bar soap components) is added to solubilize the fatty acid soap components to provide bar clarity. Thus, the transparent bar soap of the present invention is essentially free of monohydric alcohol that can dry the skin.

As previously mentioned, the major constituents of the inventive bar soap formulation include one or more of the following: (i) fatty acid soaps, (ii) humectant solvents, (iii) water, (iv) fatty acid soap solubilization aids, and (v) lathering synthetic surfactants. Each of these components is described below.

Fatty Acid Soap

The bar soap composition includes an effective amount of one or more fatty acid soaps to contribute to the cleaning and detergency properties of the bar soap. Suitable amounts of fatty acid soaps include from about 3% to about 45%, preferably from about 3% to about 20%, more preferably from about 6% to about 20%.

The fatty acid soaps include soaps derived from hydrocarbon chain lengths of from about 8 to about 22 carbons and are preferably saturated. The fatty acid soap may be the sodium-, potassium-, magnesium-, ammonium-, triethanolammonium-, alkanolammonium-(and mixtures thereof) salt of the fatty acid, preferably the sodium salt. The fatty acid soaps can be derived from purified individual chain lengths or crude mixtures, such as those derived from fats and oils (e.g., coconut, palm kernel, tallow, and triple pressed stearic). Thus, the term "fatty acid soap" includes a single fatty acid soap or a mixture of fatty acid soaps. "Stearic acid" and its fatty acid salt "stearate" are used to mean the industry standard "triple pressed stearic acid," which includes about 45% stearic and about 55% palmitic acids. Fatty acid soap derived from coconut oil (i.e, sodium cocoate) typically has a fatty acid carbon chain length distribution of about: 6% $C_8$; 6% $C_{10}$; 48% $C_{12}$; 19% $C_{14}$; 9% $C_{16}$; 3% $C_{18}$ stearic; 7% $C_{18}$ oleic; and 2% $C_{18}$ linoleic (the first six fatty acids being saturated). Fatty acid soap derived from tallow (i.e., sodium tallowate) typically has a fatty acid carbon chain length distribution of about: 3% $C_{14}$; 24% $C_{16}$ palmitic; 4% $C_{16}$ palmitoleic (saturated); 2% $C_{17}$ palmitoleic (unsaturated); 1% $C_{17}$ palmitoleic (saturated); 19% $C_{18}$ stearic; 43% $C_{18}$ oleic; 3% $C_{18}$ linoleic; 1% $C_{18}$ linolenic;

Fatty acid soaps are generally classified as "insoluble" and "soluble." As used herein, "insoluble fatty acid soap" means a salt of a saturated fatty acid having a carbon chain length of 16 to 24 that is less soluble in water than is sodium myristate; "soluble fatty acid soap" includes the remaining types of fatty acid soaps, and more particularly, salts of saturated fatty acids having a carbon chain length of 8 to 14, as well as salts of unsaturated fatty acids having a carbon chain length of 8 to 22. The solubility of sodium myristate in water at 25° C. is 0.004 molar. Preferred insoluble fatty acid soaps include sodium myristoleate, sodium palmitate, sodium palmitoleate, sodium stearate, sodium oleate, sodium ricinoleate, sodium linoleate, sodium linolenate, sodium arachidate, sodium gadoleate, sodium arachidonate, sodium behenate, sodium erucate, sodium clupanodoniate, and sodium lignocerate. Preferred soluble fatty acid soaps include sodium caprylate, sodium caprate, sodium laurate, and sodium myristate. Also preferred are fatty acid soaps that have a blend of soluble and insoluble fatty acids, such as sodium tallowate, sodium cocoate, and laurate canola oil.

In elevated amounts, insoluble fatty acid soaps tend to enhance the hardness and wear characteristics of transparent bar soap formulations containing high levels of humectant; whereas, in elevated amounts, soluble fatty acid soaps tend to enhance the clarity and foaming characteristics. A regulated balance of insoluble and insoluble fatty acid soaps also can lower the congealing point of a bar soap formulation. The "congealing point" is the temperature at which the liquid soap formulation first forms a visible solid "skin" on the surface of the cooling liquid soap formulation. Because the soap formulation is a mixture of components, the solidification of the liquid soap occurs over a temperature range (i.e., "melt point curve") that ranges from the congealing point to typically about 10° C. lower than the congealing point.

Preferably, the transparent bar soap formulation includes at least 3% insoluble fatty acid soap. The transparent bar soap formulation also preferably includes an effective balance of insoluble fatty acid soaps to soluble fatty acid soaps to provide a bar soap composition having one or more of the following attributes: (i) a hardness of from about 30 to about 100 hardness units, preferably from about 40 to about 70 hardness units, (ii) a standardized foam volume of from about 100 to about 300 milliliters, and (iii) a congealing point of from about 40° C. to about 70° C. Where the formulation includes soluble fatty acid soaps, suitable ratios of insoluble to soluble fatty acid soaps include at least about 0.4:1, preferably at least about 1:1, more preferably at least about 2:1.

Humectant Solvent

The bar soap composition includes a high level of humectant solvent to provide desired skin-moisturization and mildness attributes and to provide a vehicle in which to solubilize the fatty acid soap content of the bar soap. Suitable humectant solvent levels include from about 38% to about 96%, preferably greater than 50%, more preferably between 50% and about 96%, and most preferably between 50% and about 70%. Humectant solvents are superb skin moisturizers. However, at extremely high levels, humectant solvents may tend to reduce the foam production and contribute to the sweating phenomenon.

"Humectant solvents" include water-soluble organic polyols, such as glycerin, propylene glycol, dipropylene glycol, butylene glycol, and ethylene glycol, 1,7-heptanediol, polyethylene and propylene glycols of up to 8,000 molecular weight, and mono-$C_{1-4}$ alkyl ethers thereof, sugar alcohols such as sorbitol, mono- di- and triethanolamine, 2-amino-1-butanol, and mixtures thereof. Preferred humectant solvents are glycerin, propylene glycol, butylene glycol, and sorbitol.

As previously discussed, the humectant solvent also provides a vehicle for solubilizing the fatty acid soap content, in particular the insoluble fatty acid soap content, which is less soluble in humectant solvent than is soluble fatty acid soap. The ratio of humectant solvent to insoluble fatty acid soap preferably ranges from about 3:1 to about 23:1, more preferably from about 4:1 to less than about 14:1.

Water

Water contributes to the solvency, stabilization, processability, and moisturization characteristics of the bar soap formulation. Further, the combination of water and humectant solvent helps to reduce the tendency of a bar soap to deposit a drying film or greasy residue on the skin. Preferably, the total of the humectant solvent and water content in the bar soap formulation is at least about 65%, more preferably from about 65% to about 96%.

Fatty Acid Soap Solubilization Aid

It is desirable that upon cooling and stabilizing the bar soap formulation does not form fatty acid soap crystals that may reduce the clarity or transparency of the bar soap. Accordingly, the bar soap formulation may include at least one "soap solubilization aid" in an amount effective to assist the bar soap formulation to remain substantially free of fatty acid soap crystals, that is, free of an amount of soap crystals that noticeably reduce the clarity or transparency of the formulation during storage of the bar soap. The soap solubilization aid may also beneficially affect other characteristics, such as increasing the hardness of the bar soap and improving the foaming attributes. Generally, the longer the chain of the soap solubilization aid, the less foaming and skin irritation and the more effective fatty acid soap solubilization.

Soap solubilization aids preferably are non-ionic surfactant components that inhibit or reduce the tendency of fatty acid soap to crystallize out of the humectant solvent solution. Such soap solubilization aids include poly($C_{2-4}$alkylene) glycol ethers of $C_{12-22}$ fatty alcohols or $C_{15-26}$ alkyl phenols, where the oxyalkylene component imparts hydrophilic properties to the soap solubilization aid. The $C_{12-22}$ component may be derived from alcohols which include lauryl alcohol, myristyl alcohol, palm alcohol, stearyl alcohol, and behenyl alcohol. The alkylene group of the polyalkylene glycol portion is preferably ethylene or propylene, more preferably 1,2-ethylene or 1,2-propylene. The polyalkylene glycol portion may be a homopolymer or a mixed polymer of these alkylene oxide units. When a mixed polymer is desired, it may be a block or random copolymer. Preferably, it is an ethylene oxide homopolymer. The number of ethoxylate or propoxylate units in the soap solubilization aid (e.g., hydrophilic polyethylene glycol fatty alcohol ether) is preferably greater than 20, more preferably greater than 50, still more preferably greater than 100, even more preferably greater than 150, and most preferably at least about 175.

Examples of preferred soap solubilization aids include alkoxylated alcohols such as: (i) Pentadoxynol-200, which conforms generally to the formula $C_{15}H_{31}C_6H_4(OCH_2CH_2)_nOH$ where n averages 200, (ii) Laureth-23, and (iii) Ceteth-20. Pentadoxynol-200 is the most preferred, and is available from RTD Chemicals Corporation under the CLARIT PDP 200 trademark. Other useful soap solubilization aids include tetra(hydroxypropyl)diamine (Quadrol, BASF), 2-amino-2-methylpropanol (AMP, Angus Chemical Company), and 2-amino-2-hydroxymethyl-1,3-propanediol (Tromethamine, Sigma Chemical Company).

Useful amounts of soap solubilization aid range from about 3% to about 7%. Further, it is preferred that the ratio of insoluble fatty acid soap to soap solubilization aid is at least about 0.7:1 and that the ratio of total fatty acid soap (i.e., the combined insoluble fatty acid soap and the soluble fatty acid soap, if any) to soap solubilization aid is at least about 2:1.

Lathering Synthetic Surfactant

High humectant solvent levels in transparent bar soaps tend to lessen the desirable foaming and lathering characteristics by increasing the surface tension of the formulation. To counterbalance this effect, the transparent bar soap formulation optionally includes a lathering synthetic surfactant. The lathering synthetic surfactant preferably has a pH similar to that of human skin (e.g., a pH of from about 6 to about 7) so that it is relatively mild. Preferably, the amount of lathering synthetic surfactant is sufficient in combination with the other components of the transparent bar soap formulation to produce a standardized foam volume of at least about 100 milliliters, more preferably from about 100 milliliters to about 300 milliliters. Useful ratios of fatty acid soap to lathering synthetic surfactant include from about 3:1 to about 25:1, preferably from about 4:1 to about 7:1.

Suitable synthetic surfactants for use in the present invention include anionic, cationic, and amphoteric lathering synthetic surfactants, optionally used in conjunction with nonionic and zwitterionic synthetic surfactants.

Suitable anionic lathering synthetic surfactants include the water-soluble salts of organic, sulfonic acids and of aliphatic sulfuric acid esters, for example, those having an alkyl chain of from 10 to 22 carbon atoms and a sulfonic acid or sulfuric acid ester moiety. Examples include the sodium and potassium salts of alkyl sulfuric acids obtained from the mixed higher alcohols derived by the reduction of tallow or by the reduction of coconut oil, palm oil, palm kernel oil, palm oil stearin, babassu kernel oil or other oils of the lauric oil group. Other aliphatic sulfuric acid esters which can be suitably employed include the water-soluble salts of sulfuric acid esters of polyhydric alcohols incompletely esterified with high molecular weight soap-forming carboxylic acids. Such synthetic detergents include the water-soluble alkali metal salts of sulfuric acid esters of higher molecular weight fatty acid monoglycerides such as the sodium and potassium salts of the coconut oil fatty acid monoester of 1,2-hydroxypropane-3-sulfuric acid ester, sodium and potassium monomyristoyl ethylene glycol sulfate, and sodium and potassium monolauroyl diglycerol sulfate.

Additional useful anionic surfactants include acyl isethionates, acyl sarcosinates, alkylglycerylether sulfonates, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphonate, the alkyl ether sulfates (with 1 to 12 ethoxy groups), and mixtures thereof, wherein the surfactants contain a $C_8$ to $C_{22}$ alkyl chain and wherein the counterion is selected from the group consisting of: Na, K, $NH_4$, $N(CH_2CH_2OH)_3$.

Specific examples include sodium lauroyl sarcosinate, sodium cocoyl isethionate, sodium laureth sulfate, sodium lauryl sulfate, cocamidopropyl hydroxybetaine, cocamidopropyl hydroxysultaine, lauramide DEA, alkyl glyceryl ether sulfonate (AGS), sulfonated fatty esters, sulfonated fatty acids, alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, alkyl ether sulfates with 1 to 12 ethoxy groups (e.g., ammonium and sodium lauryl ether sulfates), and mixtures thereof.

Nonionic synthetic surfactants include alkyl glycosides, such as alkyl polyglycoside surfactants, and methyl glucose esters; decyl glucoside; polysorbates, such as polysorbate 20, polysorbate 40, polysorbate 60, polysorbate 80, and polyethylene glycol (PEG) esters, such as PEG 60 hydrogenated castor oil.

Suitable cationic lathering synthetic surfactant include alkyl trimonium chloride and methosulfate, and dialkyldimonium chloride and methyl sulphate, and alkyl alkonium chloride and methyl sulphate, and mixtures thereof. These surfactants contain $C_{12}$ to $C_{24}$ carbon atoms per alkyl chain. The most preferred cationic is selected from the group consisting of stearylkonium chloride, stearyltrimonium chloride, Di-stearyl-dimonium chloride, and mixtures thereof.

Suitable amphoteric and zwitterionic synthetic surfactants include: sultaines, for example, cocamidopropyl hydroxysultaine and lauryl hydroxysultaine; aminobetaines and amidobetaines, for example, cocoamidopropyl betaine, lauryl betaine, cetyl betaine, cocobetaine, lauramidopropyl betaine and stearamidopropyl betaine; glycinates, for example, cocoamphoglycinate and cocoamphocarboxyglycinate; and aminopropionates, for example sodium lauraminopropionate.

Other Components

The transparent moisturizing bar soap composition optionally contains one or more other additives commonly included in personal soap bars, such as perfumes, polymeric skin feel and mildness aids, fillers, sanitizing or antimicrobial agents, dyes, colorants, preservatives, and perfumes.

Compatible salt and salt hydrates can be incorporated into the transparent bar soap formulation to increase the hardness of the bar soap, preferably without changing any other attributes of the bar soap. Some preferred salts are sodium chloride, sodium sulfate, disodium hydrogen phosphate, sodium pyrophosphate, sodium tetraborate, potassium chloride, and ammonium chloride. Useful amounts of salt (e.g., sodium chloride) include from about 0.5% to about 2%, preferably about 1% salt, more preferably an amount of salt that in combination with the other bar soap components results in a hardness of about 40 to about 70 hardness units.

Manufacture

To manufacture the transparent bar soap formulation of the present invention, the humectant solvent and water components are first mixed, for example, in a mix vessel. The mix vessel should include an agitator to gently and uniformly agitate the mix components. The mix vessel should also include a heating jacket to heat the contents during mixing. Preferably, the humectant solvent and water mixture is heated from about 65° C. to about 85° C. The remaining components can be added one at a time, preferably with homogeneous mixing between additions, until all solids have dissolved. The temperature during this mixing is preferably maintained within a range of from about 50° C. to about 80° C., but above the congealing point of the mixture. Volatile ingredients, such as fragrances, are preferably added after the mixture has cooled to the lower part of this temperature range.

The fatty acid soaps for the bar formulation can be provided: (i) by adding the preformed fatty acid soap salt, or (ii) by adding the free fatty acid and a base (e.g., sodium hydroxide) to form the fatty acid soap in situ, or (iii) by saponification of triglycerides (fats and oils) in situ. The relatively moderate processing temperatures noted above are possible where the fatty acid soaps are introduced either as preformed fatty acid soaps or as free fatty acids that are neutralized in situ. Saponification generates higher temperatures that may "brown" or discolor the humectant solvent or other bar soap components. It is true that saponification has the advantage of simultaneously producing both fatty acid soaps and glycerin, a desirable humectant solvent. However, since the inventive bar soap composition may contain a relatively low amount of fatty acid soap, the in situ saponification may produce an insufficient amount of glycerin so that additional glycerin or other humectant solvent must also be added. In situ saponification must be driven to completion to assure that there is not free fatty acid or triglyceride remaining in the composition that may contribute to cloudiness.

The homogeneous bar soap formulation mixture may be poured directly into molds, trays, or containers to shape the bars (i.e., the "hot pour" or "hot fill" method). So the formulation can cool relatively quickly, as discussed below, the temperature of the pour mixture is preferably from about 2° C. to about 14° C. above the bar soap formulation's congealing point. Preferably, for formulations that congeal more quickly (i.e., formulations containing a higher ratio of insoluble fatty acid soap to soluble fatty acid soap), the temperature of the pour mixture is about 8° C. to about 14° C. above the congealing point, which helps to allow any entrained air to migrate to the surface before the poured formulation congeals.

It is also preferred that the congealing point of the bar soap formulation be relatively moderate, for example from about 40° C. to about 70° C., so that low-cost plastic molds and trays can be used with the hot pour method, rather than more expensive metal molds capable of withstanding higher temperatures.

Faster fill and congealing rates are helpful for decreasing the cost of producing the transparent bar soaps. Preferably, the molds are filled in a continuous process. The mix time for most batches can be achieved in from 3 to 5 hours, which allows a complete turnover of a batch (including cleaning the mix vessel and pre-weighing the bar soap components) within a single 8-hour shift.

After a mold or tray is filled, it is transferred to a cooling unit. The filled molds can be cooled using several different methods known in the art. For example, the filled molds can be cooled continuously at ambient room temperature or in a cooling tunnel (typically at a temperature of from 4° C. to 10° C.). The cooling tunnel can reduce the cooling time by at least about half. Alternatively, the filled molds can be aged in a refrigerator (typically at a temperature of 5° C.) for quick-cooling. The production time (and therefore costs) are dependent upon the amount of residence time required to congeal and solidify the poured bars.

The transparency or clarity of the transparent bar soap formulations of the present invention are relatively independent of the cooling rate. For example, cooling rates of from about 0.1° C. to about 1.5° C. per minute have produced transparent bars.

After cooling to solidify the bars, the solidified bars can be cut, stamped, or merely removed from the mold in the final form, as is known in the art. In a preferred embodiment, because of the bars' low temperature congealing point, the bars may be formed in a low cost plastic, HDPE, PTE or PP packaging mold, which may also serve as the bars' final package. This packaging mold includes an inlet, preferably funnelized and located at the top the mold, to (1) improve the filling of the mold with the bar soap formulation, and optionally, (2) allow air entrained in the bar soap formulation to escape from the packaging mold. The packaging mold includes three dimensional images that ultimately are reflectively incorporated into the surfaces of the congealed bars.

Preferably, the packaging mold includes two opposed forms, each having opposing perepheries. The forms are preferably joined along a portion of the peripheries by a hinge and releasably sealed around the remaining portion of the peripheries to provide a single solid mold into which the bar soap formulation may is to congeal properly in the form of the packaging mold. The hinge allows the ultimate consumer to open the package along the unhinged peripheries that is releasably sealed. Alternatively, the mold package may consist of two opposed forms that fit together along opposing peripheries to form a seal that assists in retaining the shape of the soap bar formulation as it congeals within the mold. The ultimate consumer may open the molding package to access the completed bar by breaking the seal and separating the two opposing molds.

To form the bar soap formulation in the packaging molds, the bar soap formulation is first poured into the packaging mold as discussed above through an inlet in the top of the packaging mold conventionally placed to facilitate filling the packaging mold as well as providing an escape port for air entrained in the soap formulation as it congeals. As the soap bar formulation is poured into the packaging mold, it conforms to all three dimensional shapes or images that are present in the forms of the mold. Once the packaging mold has been filled as desired, the soap-filled molding package is moved on to further packaging or processing, even before the molten soap congeals completely. The molding package is ultimately opened by the consumer to use the enclosed soap bar.

For those bars not packaged in their molds according to the preferred embodiment above, the scrap from the finishing step can be recycled by adding it to the mix vessel at a preferred amount of less than about 10% of the total batch weight. The bars can be individually packaged, such as with a plastic barrier film, to reduce the rate of weight loss or absorption of ambient water vapor. The inventive bar soap may be used as a bath or shower bar soap in the same commonly known manner as used for existing personal bar soaps to clean hands, face, and general body.

The following examples are presented for the purpose of further illustrating and explaining the present invention and are not to be taken as limiting in any regard. Unless otherwise indicated, all parts and percentages are by weight.

EXAMPLES 1–3

The following formulations had high levels of humectant in solid bar soaps.

| Component | Function | Example 1 | Example 2 | Example 3 |
| --- | --- | --- | --- | --- |
| Glycerin | humectant solvent | 72.8 | 72.8 | 95.8 |
| Water, purified | Solvent | 19.8 | 12.4 | — |
| Sodium Stearate | insoluble fatty acid soap | 7.4 | 14.8 | 4.2 |
| | Ratio of humectant/insoluble fatty acid soap | 10:1 | 5:1 | 23:1 |
| | Hardness ("hardness units") | 89 | 43 | 79 |
| | Clear/Transparent | Trans-parent | Trans-parent | Trans-parent |

The following process is used to make the soap formulations as recited in Examples 1–3. The process comprises the following steps:

1. Adding the ingredients in the following order: humectant solvent (e.g. glycerin), solvent (e.g. purified water).
2. Heating the combined ingredients, that is, the batch, to about 80° C.
3. Adding insoluble fatty acid soap (e.g. sodium stearate).
4. Mixing the ingredients until all are dissolved, typically for about 30 minutes.
5. De-aerating and pouring the soap formulation into a mold before it congeals.

Notably, Examples 1–3 displayed little tendency to foam and each tended to sweat. Glycerin levels above about 96% did not produce a bar soap.

EXAMPLES 4–6

The following formulations had lower ratios of humectant to insoluble fatty acid soap and showed the beneficial foaming effect of a lathering synthetic surfactant.

| Component | Function | Example 4 | Example 5 | Example 6 |
| --- | --- | --- | --- | --- |
| Glycerin | humectant solvent | 48.25 | 48.25 | 38.6 |
| Sorbitol | humectant solvent | — | — | 9.65 |
| Water, purified | Solvent | 20.25 | 20.25 | 20.25 |
| Sodium Stearate | insoluble fatty acid soap | 15.5 | 11.75 | 11.75 |
| Lauramide DEA | lathering synthetic surfactant | 8.0 | 11.75 | 11.75 |
| Sodium Laureth Sulfate | lathering synthetic surfactant | 3.0 | 3.0 | 3.0 |
| Cocamido-propyl Hydroxy-sultaine | lathering synthetic surfactant | 5.0 | 5.0 | 5.0 |
| | Ratio of humectant/insoluble fatty acid soap | 3:1 | 4:1 | 3.5:1 |
| | Hardness ("hardness units") | 69 | 78 | 88 |
| | Clear/Transparent | Trans-parent | Clear | Trans-parent |
| | PH | 10.5 | 10.5 | 11.0 |

The following process is used to make the soap formulations as recited in Examples 4–6. The process comprises the following steps:

1. Adding the ingredients in the order: first humectant solvent (e.g. glycerin), second humectant solvent (e.g. sorbitol), solvent (e.g. purified water).
2. Heating the added ingredients to about 85° C.
3. Adding the insoluble fatty acid soap (e.g. sodium stearate).
4. Mixing the added ingredients until they dissolve, typically for about 60 minutes.
5. Adding the remaining ingredients in the order (top to bottom) as listed in the immediately above table.
6. De-aerating and pouring the resultant soap formulation into molds before it congeals.

Example 4 had good flash foam; and Examples 5–6 had good lather foam. It was found that Examples 4–6 bars could be made harder without changing any other attributes by adding of from about 0.5% to about 2% sodium chloride. The optimum level was about 1% salt, which resulted in a hardness of from about 60 to 70 hardness units. It was also found that addition of from 0.5% to 2.0% of an acid such as citric acid to Examples 4–6 resulted in a pH of from 9.1 to 10.0. Since 2% citric acid resulted in some loss of clarity and hardness, it is preferable to add less than 2% citric acid, more preferably less than about 1% citric acid.

EXAMPLES 7–9

The following formulations had improved foaming by inclusion of lathering synthetic surfactants.

| Component | Function | Example 7 | Example 8 | Example 9 |
| --- | --- | --- | --- | --- |
| Glycerin | humectant solvent | 47.25 | 34.3 | 33.3 |
| Propylene Glycol | humectant solvent | — | 15.0 | 12.0 |
| Water, purified | solvent | 22.55 | 23.2 | 21.3 |
| Sodium Stearate | insoluble fatty acid soap | 12.5 | 11.0 | 12.0 |
| Laureth-23 | soap solubilization aid and lathering synthetic surfactant | 7.7 | 7.7 | — |
| Ceteth-20 | soap solubilization aid and lathering synthetic surfactant | — | — | 12.0 |
| Sodium Chloride | increase hardness | 1.0 | 1.0 | 1.0 |
| Sodium Laureth Sulfate | lathering synthetic surfactant | 3.0 | — | — |
| Cocamido-propyl Hydroxy-betaine | lathering synthetic surfactant | 3.0 | 3.9 | 4.2 |
| | Ratio of humectant/insoluble fatty acid soap | 3.8:1 | 4.5:1 | 3.8:1 |
| | Hardness ("hardness units") | 49 | 51 | 55 |
| | Clear/Transparent | Clear | Trans-parent | Clear |
| | pH | 9.2 | 10.0 | 10.1 |
| | Standardized wear rate | 5.3% | 9.6% | 9.7% |

The following process is used to make the soap formulations as recited in Examples 10–12. The process comprises the following steps:

1. Adding the ingredients in the order: first humectant solvent (e.g. glycerin), second humectant solvent (e.g. sorbitol), solvent (e.g. purified water).
2. Heating the batch to about 85° C.

3. Adding the insoluble fatty acid soap (e.g. sodium stearate).
4. Mixing the added ingredients until they dissolve, typically 60 minutes.
5. Adding the remaining ingredients in the order (top to bottom) as listed in the table immediately above.
6. De-aerating and pouring the soap formulation into molds before it congeals.

Example 7 was water white and had good lather foam. Examples 8–9 had good flash and lather foam.

EXAMPLES 10–12

The following formulations mixed soluble and insoluble soaps with soap solubilization aids.

| Component | Function | Example 10 | Example 11 | Example 12 |
|---|---|---|---|---|
| Glycerin | Humectant solvent | 36.9 | 38.0 | 37.5 |
| Propylene Glycol | Humectant solvent | 19.0 | 19.5 | 19.2 |
| Water, purified | Solvent | 16.2 | 17.4 | 15.9 |
| Pentadoxynol-200 | soap solubilziation aid | 5.0 | 5.0 | 5.0 |
| Sodium Stearate | Insoluble fatty acid soap | 7.5 | 4.4 | 6.8 |
| Sodium Tallowate | blend of insoluble and soluble fatty acid soaps (e.g., 49 parts/51 parts) | 8.2 | — | 4.0 |
| Sodium Cocoate | blend of insoluble and soluble fatty acid soaps (e.g., 11 parts/89 parts) | 1.4 | — | 0.8 |
| Sodium Laurate | Soluble fatty acid soap | — | 5.0 | 2.5 |
| Sodium Myristate | Soluble fatty acid soap | — | 5.0 | 2.5 |
| Sodium Lauryl Sulfate | Lathering synthetic surfactant | 5.0 | 4.9 | 5.0 |
| Fragrance & color | | 0.8 | 0.8 | 0.8 |
| | Ratio of humectant/insoluble fatty acid soap | 4.8:1 | 13.1:1 | 6.4:1 |
| | Ratio of insoluble fatty acid soap/soluble fatty acid soap | 2.2:1 | 0.4:1 | 1.1:1 |
| | Ratio of insoluble fatty acid soap/soap solubilization aid | 2.3:1 | 0.9:1 | 1.8:1 |
| | Ratio of fatty acid soap/soap solubilization aid | 3.4:1 | 2.9:1 | 3.3:1 |
| | Hardness ("hardness units") | 50 | 72 | *** |
| | Clear/Transparent | Clear | Clear | Clear |
| | PH | 9.8 | 9.5 | 9.6 |
| | Standardized wear rate | 7% | 10.0% | *** |
| | Standardized foam volume (milliliters) | 150 | 200 | 100 |

*** Not measured.

The following process is used to make the formulation as recited in Example 10. The process comprises of the following steps:

1. Adding the ingredients in the order: first humectant solvent (e.g. glycerin), second humectant solvent (e.g. sorbitol), solvent (e.g. purified water).
2. Heating the added ingredients to about 85° C.
3. Adding the soap solubilization aid (e.g. pentadoxynol-200), insoluble fatty acid soap (e.g. sodium stearate) and the blend of soluble and insoluble fatty acid soaps (e.g. sodium tallowate and sodium cocoate). When adding the soap solubilization aid, the insoluble fatty acid soap, and the blend of insoluble and soluble fatty acid soaps individually, each ingredient should be dissolved into the mixing composition and the batch should be uniform before adding the next ingredient.
4. Adding the remaining ingredients in the following order: the soluble fatty acid soaps (e.g. sodium laurate and sodium myristate), the lathering synthetic surfactant (e.g. sodium lauryl sulfate), and mixing the ingredients as they are added so that they all dissolve within the batch, typically after about 60 minutes.
5. Cooling and de-aerating the soap formulation at about 65° F.
6. Optionally adding fragrance and/or color to the composition.
7. Pouring the soap formulation into molds before it congeals.

The following process is used to make the soap formulation recited in Examples 11–12. The process comprises the following steps:

1. Adding the ingredients in the following order: first humectant solvent (e.g. glycerin), second humectant solvent (e.g. sorbitol), solvent (e.g. purified water).
2. Heating the ingredients to about 80° C.
3. Adding the soluble fatty acid soaps (e.g. sodium laurate and sodium myristate).
4. Adding the soap solubilization aid (e.g. pentadoxynol-200) and the insoluble fatty acid soap (e.g. sodium stearate). Simultaneously, while adding these ingredients, insuring that each ingredient has dissolved and the batch is uniform before adding the next ingredient.
5. Adding the remaining ingredients in the following order: the blend of insoluble and soluble fatty acid soaps (e.g. sodium tallowate and sodium cocoate) and the lathering synthetic surfactant (e.g. sodium lauryl sulfate).
6. Mixing all the ingredients until dissolved, typically for about 60 minutes.
7. Cooling and de-aerating the soap formulation at about 55° F.
8. Optionally adding fragrance and color.
9. Pouring the resultant soap formulation into molds before it congeals.

Examples 10–12 were very clear and almost water white. Example 10 had good lather foam; Example 11 had good flash foam; and Example 12 had both good flash and lather foam characteristics. Example 10 had a congealing point of about 55° C. and was a free-flowing liquid above 57° C.; thus, Example 10 could be supplied continuously to molds as long as the system temperature was above 57° C. Example 11 had a congealing temperature of about 43° C. and a free-flowing temperature of about 48° C. Examples 10–12 were substantially free from fatty acid soap crystals.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. As used in the specification, the term "includes" or "including" is understood to mean "includes but is not limited to." Except in the claims and the specific examples, or where otherwise expressly indicated, all numerical quantities in this description indicating amounts of material, reaction conditions, use conditions, molecular weights, and/or number of carbon atoms, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated. Unless otherwise expressly indicated, all percentages in the claims are weight percentages based on the total weight of the composition.

The embodiments of the invention in which an exclusive property or privilege is claimed are defined as follows:

1. A method for manufacturing and shipping a soap bar comprising:

forming a homogeneous liquid mixture including greater than about 55% humectant solvent and no added monohydric alcohol;

transferring the homogeneous liquid mixture to a packaging mold including an interior having a three-dimensional image disposed therein to form a soap bar reflectively incorporating the three-dimensional image; and shipping the soap bar in the packaging mold.

2. The method of claim 1 wherein the packaging mold is constructed of a material selected from the group consisting of high density polyethylene, polypropylene and polyethylene terephthalate.

3. The method of claim 1 comprising cooling the homogeneous liquid mixture.

4. The method of claim 3 wherein the homogeneous liquid mixture is cooled at ambient temperature.

5. The method of claim 3 wherein the homogeneous liquid mixture is cooled with refrigeration.

6. The method of claim 3 wherein the homogeneous liquid mixture congeals at about 40° C. to about 70° C.

7. A method for manufacturing a transparent soap bar having no added alcohol comprising:

forming a homogeneous liquid mixture including one or more fatty acid soaps and one or more humectant solvents, the humectant solvents present in an amount greater than about 55%;

transferring the homogeneous liquid mixture to a mold or a tray; and cooling the homogeneous mixture to form a transparent solid soap bar having a standardized wear rate of less than about 15% and a hardness of about 30 to about 100 hardness units wherein the mold or tray is the final packaging of the solid soap bar.

8. The method of claim 7 wherein the homogeneous mixture includes from about 3% to about 20% of one or more fatty acid soaps, wherein the amount of insoluble fatty acid soap is at least about 3%.

9. The method of claim 7 comprising maintaining the temperature of the homogeneous liquid mixture at or below about 85° C. during the forming step.

10. The method of claim 7 wherein the weight ratio of humectant solvent to insoluble fatty acid soap ranges from about 3:1 to about 23:1.

11. The method of claim 7 comprising shipping the transparent soap bars in the mold or tray.

12. The method of claim 7 comprising maintaining the temperature of homogeneous liquid mixture at from about 2° C. to about 14° C. above the congealing point of the mixture during the transferring step.

13. The method of claim 7 wherein the mold or tray includes an inlet through which the homogeneous liquid mixture is poured.

14. The method of claim 13 wherein the mold or tray includes opposed first and second forms, the first form having a first periphery, the second form having a second periphery, the first periphery being partially sealed to the second periphery whereby the homogeneous liquid mixture is prevented from leaking out from the mold or tray.

15. The method of claim 14 wherein the first and second forms are hinged together along a portion of the first and second peripheries.

16. The method of claim 15 wherein the mold or tray may be hingedly opened by a consumer.

17. The method of claim 16 comprising shipping the soap bar in the mold or tray.

18. The method of claim 7 further comprising de-aerating the homogeneous liquid mixture.

19. A method for forming and packaging a transparent soap bar comprising:

forming a homogeneous liquid mixture at or below about 85° C. including a humectant solvent in an amount of from about 38% to about 96%;

transferring the homogeneous liquid mixture to a plastic packaging mold to fill the packaging mold, the mold including a three-dimensional interior conforming to the exterior of a whole soap bar; and cooling the transferred homogeneous liquid mixture in the mold to form a transparent solid soap bar.

20. A soap bar conforming substantially to three-dimensional interior surfaces of a mold in which the soap bar is packaged, made by the process comprising:

forming a homogeneous liquid mixture including a humectant solvent in an amount of from about 38% to about 96%;

pouring the homogeneous liquid mixture into a mold to completely fill the mold whereby the homogeneous liquid mixture conforms to the three-dimensional interior surface features of the mold; and cooling the homogeneous liquid mixture to form a soap bar packaged in the mold in which the soap bar is formed.

* * * * *